United States Patent
Norman

(10) Patent No.: US 11,878,091 B2
(45) Date of Patent: *Jan. 23, 2024

(54) METHODS FOR PROTECTING A PARATHYROID

(71) Applicant: James Glenn Norman, Tampa, FL (US)

(72) Inventor: James Glenn Norman, Tampa, FL (US)

(*) Notice: Subject to any disclaimer, the term of this patent is extended or adjusted under 35 U.S.C. 154(b) by 443 days.

This patent is subject to a terminal disclaimer.

(21) Appl. No.: 17/162,032

(22) Filed: Jan. 29, 2021

(65) Prior Publication Data

US 2021/0146009 A1     May 20, 2021

Related U.S. Application Data

(63) Continuation of application No. 16/425,578, filed on May 29, 2019, now Pat. No. 10,933,164, which is a continuation-in-part of application No. 16/219,038, filed on Dec. 13, 2018, now Pat. No. 10,342,631.

(51) Int. Cl.
| | | |
|---|---|---|
| A61L 27/38 | (2006.01) | |
| A61K 35/50 | (2015.01) | |
| A61K 35/28 | (2015.01) | |
| A61K 35/51 | (2015.01) | |
| A61K 35/14 | (2015.01) | |
| A61K 35/35 | (2015.01) | |

(52) U.S. Cl.
CPC .......... *A61L 27/3839* (2013.01); *A61K 35/28* (2013.01); *A61K 35/50* (2013.01); *A61K 35/51* (2013.01); *A61L 27/3834* (2013.01); *A61K 35/14* (2013.01); *A61K 35/35* (2013.01)

(58) Field of Classification Search
CPC ........ A61K 35/28; A61K 35/50; A61K 35/51; A61K 35/55; C12N 5/0617; A61B 90/04; A61L 27/3834; A61L 27/3839
See application file for complete search history.

(56) References Cited

U.S. PATENT DOCUMENTS

| | | | |
|---|---|---|---|
| 7,044,965 B1 * | 5/2006 | Spielberg | A61F 2/915 623/1.42 |
| 10,342,631 B1 | 7/2019 | Norman | |
| 10,869,953 B2 * | 12/2020 | Norman | A61L 27/3834 |
| 10,933,164 B2 * | 3/2021 | Norman | A61L 27/3839 |
| 2004/0181240 A1 * | 9/2004 | Tseng | A61L 27/3882 606/119 |
| 2016/0082152 A1 | 3/2016 | Brahm | |

FOREIGN PATENT DOCUMENTS

WO     2017165698 A1     9/2017

OTHER PUBLICATIONS

"The Pursuit of Regenerative Healing", date unknown, retrieved from https://amnioxmedical.com/human-amniotic-membrane/, 4 pages.
(Continued)

*Primary Examiner* — William H Matthews
(74) *Attorney, Agent, or Firm* — Thompson Coburn LLP

(57) ABSTRACT

A method includes covering or contacting a portion of a parathyroid of a subject with a shield including extraembryonic tissue and/or a stem cell. The covering or contacting occurs during a neck or reconstructive surgery of the subject.

25 Claims, 4 Drawing Sheets

(56) References Cited

OTHER PUBLICATIONS

Actishield Amniotic Barrier Membrane, date unknown, retrieved from http://www.wright.com/products-biologics/actishield, 2 pages.
Allen et al., "Augmented Dried Versus Cryopreserved Amniotic Membrane as an Ocular Surface Dressing", PLOS One, 2013, 15 pages, vol. 8, No. 10.
Amnioexcel, Derma Sciences, date unknown, retrieved from http://www.dermasciences.com/amnioexcel, 4 pages.
Amniograft, Biotissue, date unknown, retrieved from http://www.biotissue.com/products/amniograft.aspx, 2 pages.
Avtec Surgical online catalog, SteriShield II Dual Layer Amnion Membrane (10mm × 25mm), date unknown, retrieved from https://www.bonegrafting.com/dual-layer-amnion-membrane-81025, 2 pages.
Biovance Human Amniotic Membrane Allograft, date unknown, retrieved from https://www.woundsource.com/product/biovance-human-amniotic-membrane-allograft, 6 pages.
Caglia et al., "Post-Thyroidectomy Hypoparathyroidism, What Should we Keep in Mind?", Annali Italiani di Chirurgia, 2017, pp. 371-381, vol. 88, No. 5.
Deniwar et al., "Electrophysiological Neural Monitoring of the Laryngeal Nerves in Thyroid Surger: Review of the Current Literature", Gland Surgery, 2015, pp. 368-375, vol. 4, No. 5.
Joliat et al., "Recurrent Laryngeal Nerve Injury After Thyroid and Parathyroid Surgery", Medicine, 2017, 5 pages, vol. 96, No. 17.
Orloff et al., "American Thyroid Association Statement on Postoperative Hypoparathyroidism: Diagnosis, Prevention, and Management in Adults", Thyroid, 2018, pp. 830-841, vol. 28, No. 7.
Pawitan, "Prospect of Stem Cell Conditioned Medium in Regenerative Medicine", Biomedical Research International, 2014, 14 pages, vol. 2014.
Snyder et al., "Elucidating Mechanisms of Recurrent Laryngeal Nerve Injury During Thyroidectomy and Parathyroidectomy", Journal of American College of Surgeons, 2008, pp. 123-130, vol. 206.
Su et al., "Risk Factors of Hypoparathyroidism Following Total Thyroidectomy with Central Lymph Node Dissection", Medicine, 2017, 6 pages, vol. 96, No. 39.
Surforce product flyer, "Cryopreserved Amniotic Membrane Allograft", 2 pages.
Surgraft, Dehydrated Amniotic Membrane Sheet Biological Protective Covering to Aid in Wound Management, brochure, date unknown, 2 pages.
Teshima et al., "Postoperative Hypoparathyroidism After Total Thyroidectomy for Thyroid Cancer", Auris Nasus Larynx, 2018, pp. 1233-1238, vol. 45.
Zagoura et al., "Therapeutic Potential of a Distinct Population of Human Amniotic Fluid Mesenchymal Stem Cells and Their Secreted Molecules in Mice with Acute Hepatic Failure", Gut, 2012, pp. 894-906, vol. 61, No. 6.
"Society of Robotic Surgery Annual Meeting 2018, Stockholm, Sweden", Journal of Robotic Surgery, 2018, pp. 581-602, vol. 12, No. 3.
Carling, "Protection of Laryngeal Nerve Palsy Using Amniotic Membrane Shield During Thyroid Surgery", Endocrine, 2021, pp. 197-199, vol. 74, No. 1.
Christison-Lagay et al., "Complications in Head and Neck Surgery", Seminars in Pediatric Surgery, 2016, pp. 338-346, vol. 25, No. 6.
Litwiniuk et al., "Amniotic Membrane: New Concepts for an Old Dressing", Wound Repair and Regeneration, 2014, pp. 451-456, vol. 22, No. 4.
Moley et al., "Preservation of the Recurrent Laryngeal Nerves in Thyroid and Parathyroid Reoperations", Surgery, Oct. 1999, pp. 673-679, vol. 126, No. 4.

* cited by examiner

METHODS FOR PROTECTING A PARATHYROID

CROSS-REFERENCE TO RELATED APPLICATIONS

This application is a continuation of U.S. patent application Ser. No. 16/425,578, filed May 29, 2019 and incorporated herein by reference in its entirety, which is a continuation-in part of U.S. patent application Ser. No. 16/219,038, filed Dec. 13, 2018 and now U.S. Pat. No. 10,342,631, which is incorporated herein by reference in its entirety.

STATEMENT REGARDING FEDERALLY SPONSORED RESEARCH OR DEVELOPMENT

Not Applicable.

APPENDIX

Not Applicable.

BACKGROUND

During neck surgeries, such as surgeries on the thyroid, parathyroid, esophagus, trachea, larynx, pharynx, cervical spine, cervical lymph nodes, and carotid arteries, the recurrent laryngeal nerve is subject to damage. For example, the recurrent laryngeal nerve may be damaged as a result of trauma, desiccation, or the like. As the recurrent laryngeal nerve is typically exposed early in operations and is often the most superficial structure in the operative field, it is at risk for injury during the remainder of the operation and then during the healing phase where it remains the most superficial structure at the healing interface. Once exposed, the nerve is subject to damage from direct and indirect insults which occur during the natural course of operating and dissecting the adjacent tissues from touching, traction, stretching, friction, desiccation and even inadvertent trauma from surgical instruments. As the operative field is kept dry using suction devices or the like, the nerve is subject to damage from desiccation or the physical act of keeping the operative field dry using absorbent sponges and the use of suction apparatus. Once exposed it is also highly subject to injury from thermal or electric injury from cautery devices used in nearby tissues. Such damage adversely affects patients as the recurrent laryngeal nerve is required for phonation and speech. Patients who incur damage to the recurrent laryngeal nerve may lose their voice for a minimum of 10-12 weeks and approximately 8-10% of patients may have a permanent injury that does not improve. Patients with an injured recurrent laryngeal nerve cannot talk normally. They can speak only in a whisper. Patients with an injured recurrent laryngeal nerve also frequently aspirate liquids as they cannot adequately protect their trachea from food/liquids entering their trachea.

Injury to the recurrent laryngeal nerve is known to occur in a significant percentage of head and neck operations. To mitigate or reduce the chance of injury to the recurrent laryngeal nerve, many maneuvers are undertaken by surgeons, but to date, there has been no decrease to this risk.

During total thyroidectomy the four parathyroid glands are necessarily dissected and disturbed as the parathyroid glands are typically immediately adjacent or attached to the thyroid gland itself. It is expected that at least one, and often multiple parathyroid glands become ischemic as their blood supply is disturbed. The incidence of hypoparathyroidism (lack of parathyroid function) following total thyroidectomy is between 20 and 75%, depending on the willingness of the surgeon to measure the parathyroid function in the postoperative period. Clinically significant hypoparathyroidism requiring extended hospitalization and prolonged treatment with high levels of calcium supplementation is expected to occur in 12 to 20% of all total thyroidectomies. In a large retrospective study published in 2018, transient hypoparathyroidism occurred in 68% of patients and permanent hypoparathyroidism occurred in 18% (Teshima M, et al., Auris Nasus Larynx. 2018 December; 45(6):1233-1238. doi: 10.1016/j.anl.2018.04.008). Transient hypoparathyroidism is a very significant complication while permanent hypoparathyroidism can be life changing and debilitating (Caglia P, et al. Ann Ital Chir. 2017; 6:371-381; Orloff L A, et al. Thyroid. 2018 July; 28(7):830-841. doi: 10.1089/thy.2017.0309). Similarly, during a parathyroid exploration, the parathyroid glands are necessarily dissected and disturbed as the surgeon searches for each gland and then determines which of the four glands are enlarged. The very act of searching for and then dissecting out each parathyroid gland can make a normal, small parathyroid gland ischemic in the same way that identifying them during thyroid surgery will do. The incidence of one or more ischemic parathyroid glands following parathyroid surgery is between 20 and 80% depending on how extensive the operation is and how determined the surgeon is to find all four parathyroid glands.

Hypoparathyroidism is the most common complication following thyroid surgery and parathyroid surgery (e.g., following thyroidectomy or during parathyroid surgery) is the most common complication following thyroid surgery and results in a dramatic increase in patient morbidity and the overall cost of the procedures. As such, many maneuvers have been suggested to assure the best possible chance for damaged parathyroid glands to regain their function once they have been injured. Damaged parathyroid glands are very easy to recognize as they become dark red, purple and even near black even though their attachments to their surrounding tissues remain intact. Often the glands are not dead, but severely ischemic for a period of time (weeks or months) and thus may eventually regain function. Typically, and most commonly, surgeons will completely remove a parathyroid gland that appears ischemic so he/she can "autotransplant" the gland. This is typically done by removing the gland from the neck, cutting it into multiple very small pieces and then inserting them into a pocket developed in a muscle. Unfortunately, this maneuver guarantees this gland is non-functioning for at least 2-3 months and possibly dooming it to death and non-function forever. In fact, one of the main predictors of hypoparathyroidism is autotransplant of one or more parathyroid glands by the surgeon (Su A, et al. Medicine (Baltimore). 2017 September; 96(39):e8162. doi:10.1097/MD.0000000000008162).

Improved procedures and materials for protecting parathyroid glands are provided herein that can result in a significant decrease in the length of time for patients to return to normal parathyroid function.

SUMMARY

An aspect of the disclosure is a method comprising covering a portion of a recurrent laryngeal nerve of a subject with a shield comprising extraembryonic tissue. The covering occurs during a neck surgery of the subject.

Another aspect of the disclosure is a method comprising exposing a recurrent laryngeal nerve of a subject during a neck surgery of the subject, and covering a portion of the exposed recurrent laryngeal nerve with a shield comprising amniotic tissue.

Still another aspect of the disclosure is a shield for protecting a recurrent laryngeal nerve of a subject during a surgical procedure. The shield comprises a layer of extraembryonic tissue having a first end edge, a second end edge, a first end margin adjacent the first end edge, a second end margin adjacent the second end edge, an intermediate region between the first and second end margins, a first curved side edge extending between the first and second end edges, and a second curved side edge extending between the first and second end edges. The shield diverges away from the first end edge and toward the second end edge.

Still another aspect of the disclosure is a method comprising covering a portion of a recurrent laryngeal nerve of a subject with a shield comprising biologic tissue, wherein the neck surgery comprises performing a procedure on the subject after covering the portion of the recurrent laryngeal nerve with the shield. The procedure comprises performing surgery on one or more of a thyroid, parathyroid, esophagus, trachea, larynx, pharynx, cervical spine, cervical lymph node, or carotid artery.

In another aspect of the disclosure is a method comprising performing a neck surgery on a subject; during the neck surgery, performing a procedure on a thyroid, parathyroid, or both the thyroid and parathyroid of the subject; during the neck surgery, covering a parathyroid gland of the subject with extraembryonic tissue. In certain embodiments, the methods further comprise contacting the parathyroid gland with a stem cell, a stem cell exudate, or a combination thereof.

Still another aspect of the disclosure is a method comprising exposing a parathyroid gland of a subject, and contacting the exposed parathyroid gland with extraembryonic tissue. In certain embodiments, the methods further comprise contacting the parathyroid gland with a stem cell, a stem cell exudate, or a combination thereof.

Still another aspect of the disclosure is a method comprising exposing a parathyroid gland of a subject; contacting the parathyroid gland with a stem cell, a stem cell exudate, or a combination thereof.

These are merely some of the innumerable aspects of the present disclosure and should not be deemed an all-inclusive listing of the innumerable aspects associated with the present disclosure. These and other aspects will become apparent to those skilled in the art in light of the following disclosure and accompanying drawings. The description and specific examples in this summary are intended for purposes of illustration only and are not intended to limit the scope of the present disclosure.

BRIEF DESCRIPTION OF THE DRAWINGS

The accompanying drawings, which are incorporated in and form a part of the specification, illustrate the embodiments of the present disclosure and together with the description, serve to explain the principles of the disclosure.

Figure 1:
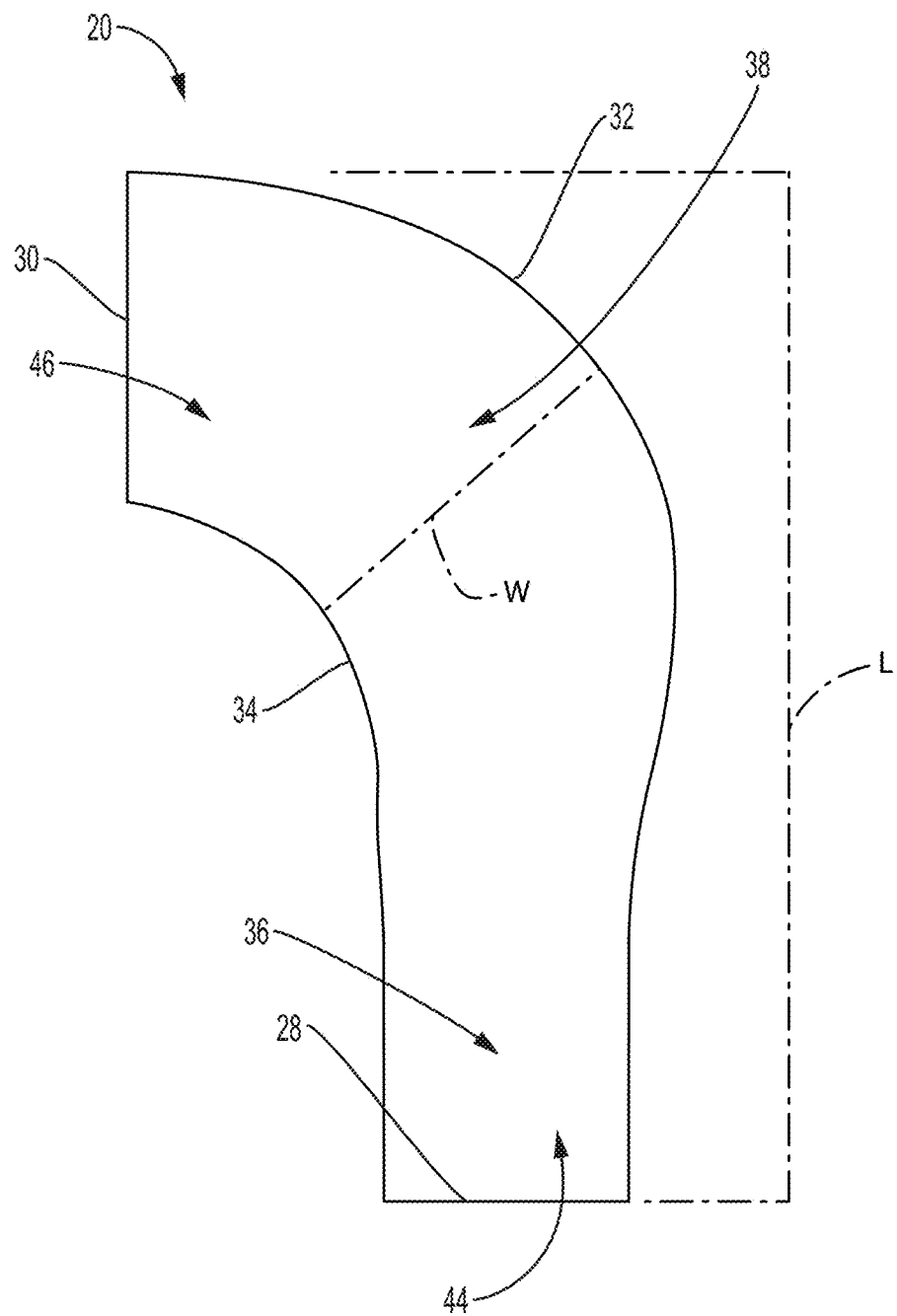
FIG. 1 illustrates a schematic top down view of one embodiment of a shield for a recurrent laryngeal nerve.

Reference characters in the written specification indicate corresponding items shown throughout the drawing figures.

DETAILED DESCRIPTION

Figure 3:
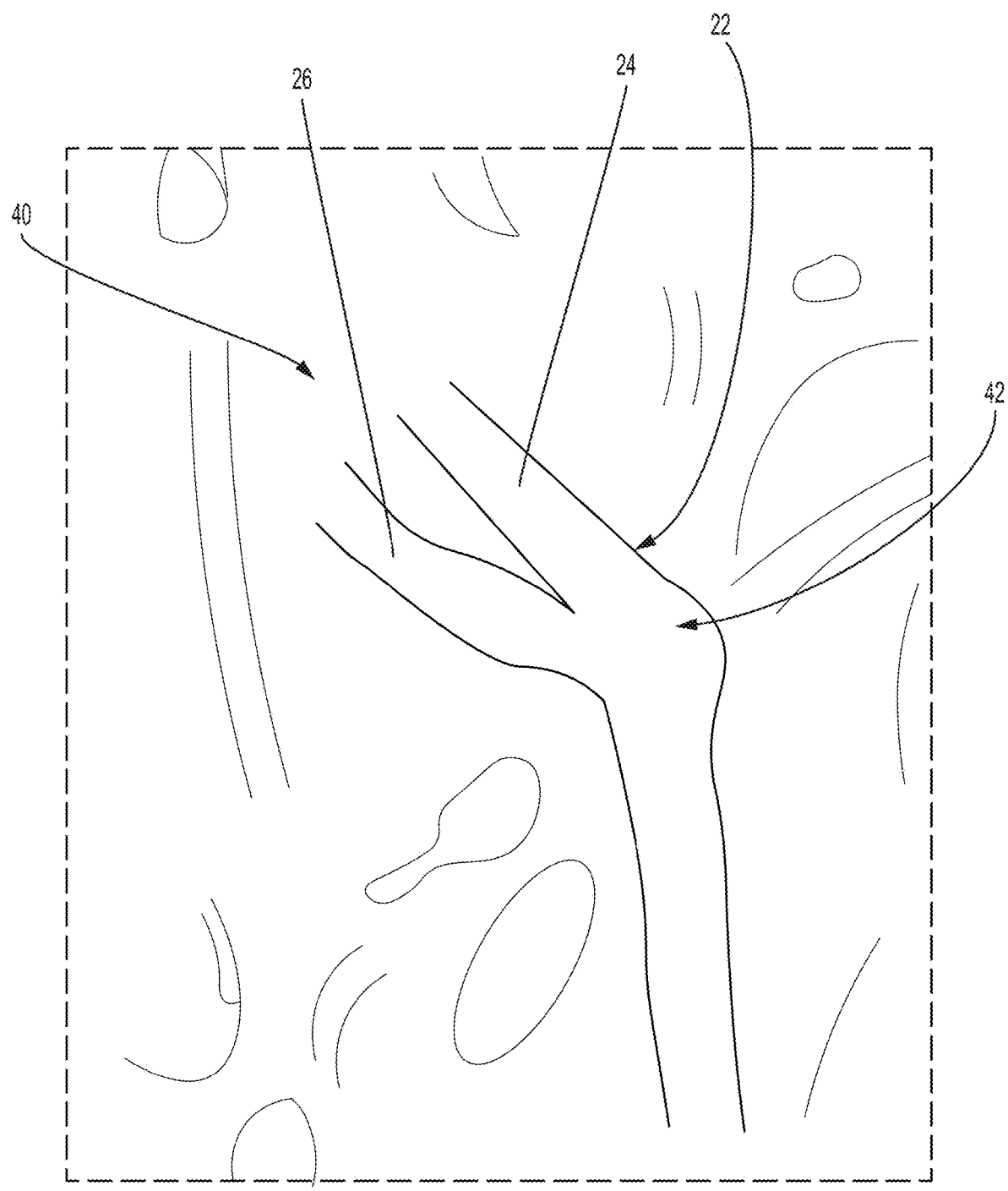
FIG. 3 illustrates a schematic view of a thyroid and exposed recurrent laryngeal nerve.
Figure 4:
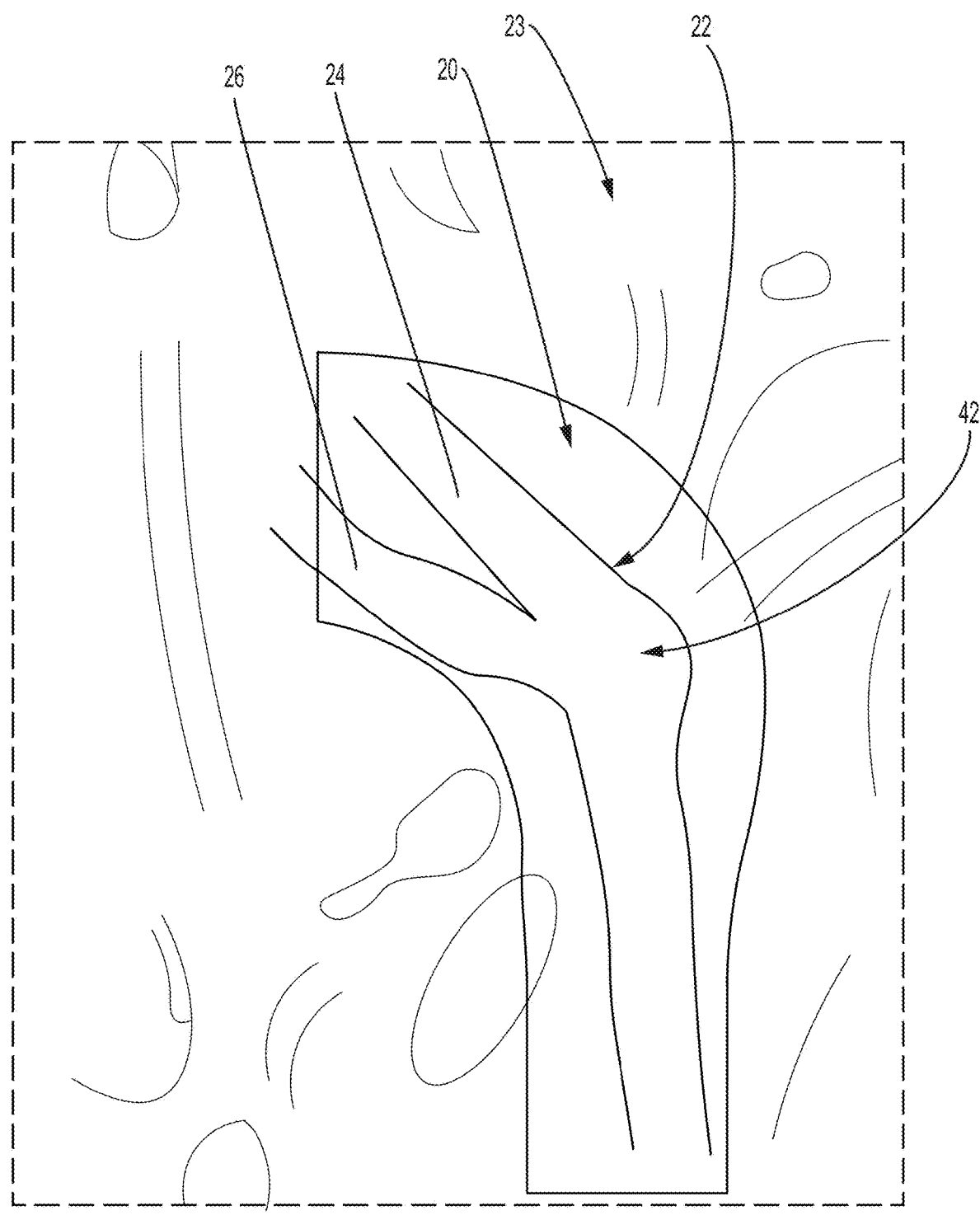
FIG. 4 illustrates a schematic view of the shield of FIG. 1 as applied to the recurrent laryngeal nerve of FIG. 3.

Referring to FIGS. 1, 3, and 4, a shield 20 for protecting a recurrent laryngeal nerve 22 is shown according to one embodiment. The shield 20 is shaped to correspond to the shape and structure of the recurrent laryngeal nerve 22 (e.g., adjacent the thyroid 23). The shape of the shield 20 accommodates the branching of the recurrent laryngeal nerve 22 into an external branch 24 and an internal branch 26. The shape of the shield 20 permits the recurrent laryngeal nerve 22 to maintain its normal, pre-surgical shape while being protected by the shield 20. This shape of the shield 20 negates the need to straighten or otherwise manipulate the recurrent laryngeal nerve 22 to cover it with the shield. This is advantageous because manipulating the recurrent laryngeal nerve 22 may damage the nerve and/or cause scarring. The shaped nature of the shield 20 may provide a further advantage in that the shield need not be shaped to fit the recurrent laryngeal nerve 22. For example, the shield 20 may be of a material that is fragile and susceptible to tearing, bunching, or the like. A rectangular, square, or other such shape that is not tailored to the recurrent laryngeal nerve may bunch up during application over the recurrent laryngeal nerve complicating positioning. The shield may bunch up and adhere to itself such that the shield cannot cover the recurrent laryngeal nerve.

In some embodiments, a parathyroid gland can be covered or contacted with a shield comprising amniotic tissue. A shield comprised of amniotic tissue that is configured to cover or contact a parathyroid gland can be in the form of a square, rectangle, a circle, oblong, or irregular shape. In general, such squares, rectangles, circles, oblongs, or irregular shapes can be at least about 1 centimeter (cm) square, at least about 1 centimeter in width (for a rectangle or oblong), or about 1 centimeter in diameter (for a circle). Examples of shields that can be used to cover or contact a parathyroid gland include but are not limited to squares of from 0.5 cm×0.5 cm to 2 cm×2 cm, or rectangles or oblongs of from 0.5 cm to 2 cm×0.5 cm to 2 cm, or circles having diameters of from about 0.5 cm to 2 cm.

In some embodiments, the shield 20 or parathyroid gland shield comprises extraembryonic tissue. For example, the shield 20 or parathyroid gland shield may be entirely or partially of human amniotic tissue. The shield 20 or parathyroid gland shield may be of commercially available amniotic tissue such as Surgraft® Dehydrated Amniotic Sheet, BIOVANCE® Human Amniotic Membrane Allograft, AMNIOEXCEL® Amniotic Allograft Membrane, Biotissue® AmnioGraft®, AMNIOX® amniotic membrane products, or Wright™ ACTISHIELD™. In alternative embodiments, the shield is of one or more of human amniotic tissue, human chorionic tissue, animal amniotic tissue, or animal chorionic tissue. For example, the shield 20 or parathyroid gland shield may comprise a combination of human amniotic tissue and human chorionic tissue.

In still further alternative embodiments, the shield 20 is of biologic tissue suitable for protecting the recurrent laryngeal nerve 22 or the parathyroid gland shield is suitable for protecting a parathyroid gland. The biologic tissue may have one or more of the following characteristics: (1) man-made biologic; (2) surface roughness (e.g., mean roughness Ra or root mean square roughness RMS) of not more than 200% greater than that of suitable human amniotic tissue, and more preferably of not more than 50% greater than that of suitable human amniotic tissue, and even more preferably of not more than 25% greater than that of suitable human amniotic tissue (where suitable human amniotic tissue constitutes any of the following commercially available products: Surgraft® Dehydrated Amniotic Sheet, BIOVANCE® Human Amniotic Membrane Allograft, AMNIOEXCEL® Amniotic Allograft Membrane, Biotissue® AmnioGraft®, AMNIOX® amniotic membrane products, and Wright™ ACTISHIELD™); (3) dissolvable or absorbable within a few days; (4) thin (e.g., have a thickness such that the tissue is translucent or transparent); (5) malleable; (6) transparent; (7) translucent; (8) non-inflammatory; (9) non-immunogenic such that it poses little if any risk of foreign body reaction; and (10) flexible such that the tissue takes on the shape of surrounding tissue (e.g., the tissue retains the general curved shape but is sufficiently flexible to conform to the tissues on which the tissue lays). In still further embodiments, the shield 20 or parathyroid gland shield comprises a combination of biologic tissue and other tissue (e.g., human amniotic tissue, human chorionic tissue, animal amniotic tissue, and/ or animal chorionic tissue).

The shield 20 may comprise compounds and/or materials to assist in protection of the recurrent laryngeal nerve 22 and/or assist in healing of the recurrent laryngeal nerve and/or surrounding tissues following the procedure. Similarly, the parathyroid gland shield may comprise compounds and/or materials to assist in protection of the parathyroid gland and/or assist in healing of the parathyroid gland and/or surrounding tissues following the procedure. For example, and without limitation, the shield may comprise an extracellular Matrix (ECM), growth factors, fibronectin, proteoglycans, laminin, and/or other proteins. The shield 20 or parathyroid gland shield may downregulate TGF-B, inhibit MMP's, suppress inflammatory cytokines, promote angiogenesis, suppress cell death (e.g., parathyroid gland cell death), and/or decrease fibroblast formation.

Regardless of material, the shield 20 or parathyroid gland shield is typically cut from a sheet of the material before it is provided to a surgeon. This allows a surgeon to use the shield 20 or parathyroid gland shield without cutting out the shield from a sheet which takes time and can be difficult to do without damaging the material. The shield 20 or parathyroid gland shield may be cut from a sheet of material during a manufacturing process using a die cutting system or the like. This provides for more accurate shaping and a reduction in damage to the shield material in comparison to other techniques such as using scissors or a scalpel to cut the shape of the shield. Typically, the sheet will be of a relatively uniform thickness resulting in a shield 20 or parathyroid gland shield having a relatively uniform thickness. For example, and without limitation, the thickness of the shield 20 or parathyroid gland shield does not deviate at any one point more than 20% from the average thickness of the shield.

The shield 20 protects the recurrent laryngeal nerve 22 from rubbing and/or friction. The shield 20 further protects the recurrent laryngeal nerve 22 from desiccation by covering the nerve. The shield 20 further protects the recurrent laryngeal nerve 22 from electrical injury from instruments by providing an insulating layer and/or alternative electrical path. The shield 20 still further protects the recurrent laryngeal nerve 22 from bacteria or other pathogens by serving as a barrier when applied. When constructed of amnion, the shield 20 may further have anti-bacterial properties in addition to forming a barrier.

As shown in FIGS. 1 and 4, the shape of the shield 20 includes several features to accommodate the recurrent laryngeal nerve 22 to provide at least the benefits described herein (e.g., being shaped to match the recurrent laryngeal nerve 22 such that the shield's dimensions need not be modified before being applied to the recurrent laryngeal nerve 22). The shield 20 includes a first end edge 28 and a second end edge 30 opposite the first end edge 28. The shield 20 diverges away from the first end edge 28 and toward the second end edge 30. A first curved side edge 32 extends between the first 28 and second 30 end edges, and a second curved side edge 34 extends between the first 28 and second 30 end edges. Resulting from the divergence, the shield 20 includes a narrow region 36 and a flared region 38. The narrow region 36 is narrower than the flared region 38. The second end edge 30 of the flared region extends adjacent the larynx 40 of the subject when the shield is applied to the recurrent laryngeal nerve 22. The external 24 and internal 26 branches of the recurrent laryngeal nerve 22 enter the larynx 40, and the second end edge 30 and the shield 20 are shaped such that the second end edge 30 is adjacent the larynx 24 and the flared region 38 covers the branching of the recurrent laryngeal nerve 22. The curvature of each of the first and second curved side edges 32, 34 follows the curvature of the upper aspect 42 of the recurrent laryngeal nerve 22.

The shield 20 has a length L of between 3.5 centimeters and 4.5 centimeters, inclusive. In some embodiments, the length L is approximately 4 centimeters. In some embodiments, the shield 20 has a maximum width W of between 0.5 centimeters and 1.5 centimeters, inclusive. In some embodiments, the maximum width W is approximately 1 centimeter. The shield 20 is sized to overlay and cover the recurrent laryngeal nerve 22. In some embodiments, the shield 20 is sized such that the shield 20 overlays either side of recurrent laryngeal nerve 22 by approximately 2-4 millimeters. The overlay allows the shield 20 to adhere to the underlying tissues as a result of water surface tension and to move with the recurrent laryngeal nerve 22 rather than move across or separately from the underlying tissues.

It should be noted that ideally the shield 20 is reversible such that the shield 20 may be applied to either a right or a left recurrent laryngeal nerve 22. The shield 20 may be flipped over as needed to align with either nerve. Alternatively, the shield 20 may be available in a right or left version.

Figure 2:
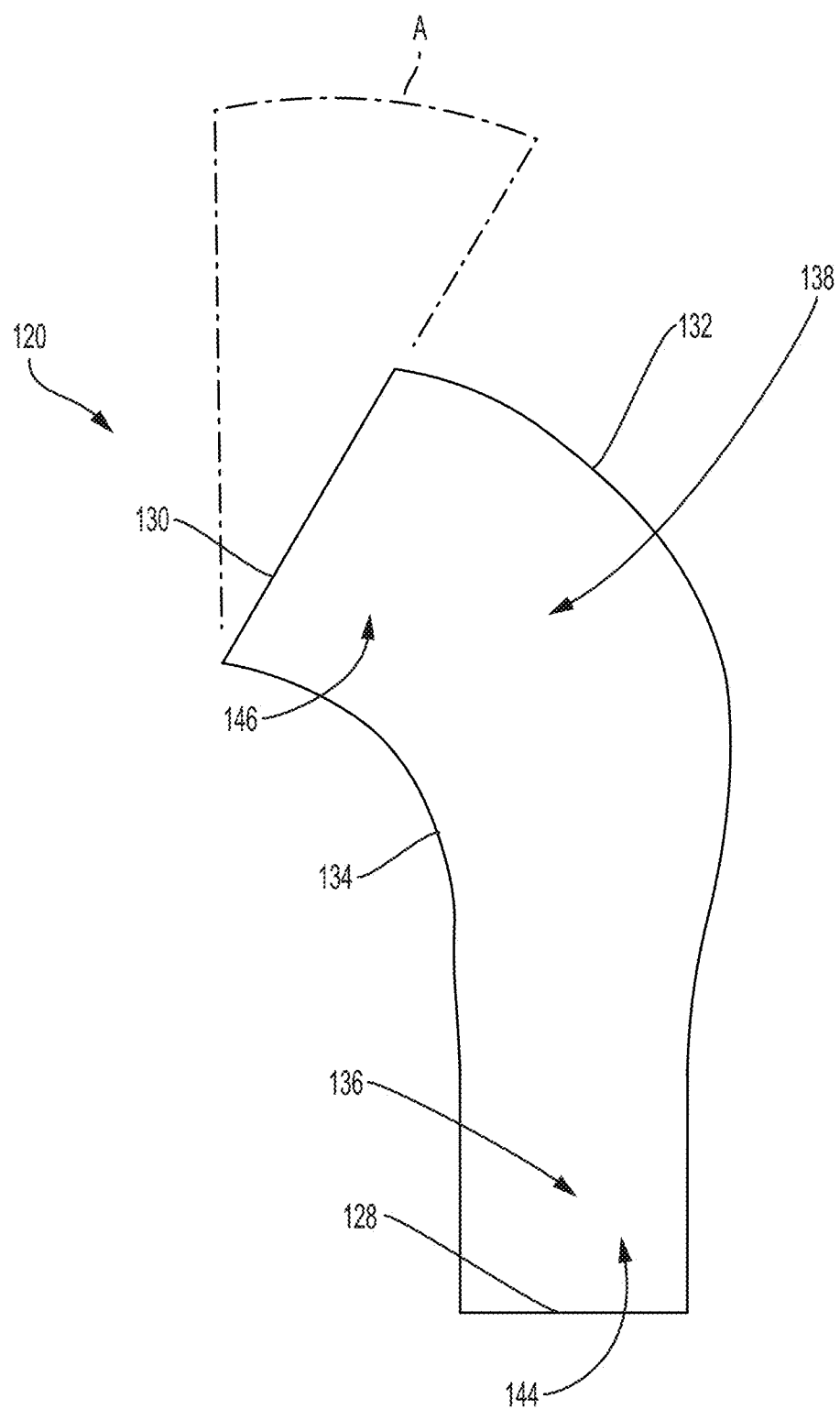
FIG. 2 illustrates a schematic top down view of an alternative embodiment of a shield for a recurrent laryngeal nerve.

Referring now to FIG. 2, an alternative embodiment of a shield 120 is shown. The shield 120 is similar to or the same as the shield 20 discussed with reference to FIG. 1 with like part numbers referring to like features (e.g., the first end edge 28 is the same as the first end edge 128). The shield 120 includes a second end edge 130 that extends along a 30 degree angle A that corresponds to the typical angle of the recurrent laryngeal nerve 22 as it enters the larynx 40.

Referring to FIG. 4, the shield 20 or 120 is used in covering a portion of the recurrent laryngeal nerve 22 of a subject. Advantageously, the shield 20 is provided pre-cut to the surgeon for use in protecting the recurrent laryngeal nerve such that the handling of the shield is reduced. In some embodiments, the shield 20 is provided to a surgeon as a part of a kit for use with a procedure of the type described herein. In one embodiment, the kit includes the shield 20 for covering the recurrent laryngeal nerve and a cotton tip swab for applying the shield. The cotton tip swab be treated or otherwise pre-prepared to be adapted for use with the shield. For example, the cotton tip swab may be a sterilized cotton tip swab.

The covering of the recurrent laryngeal nerve occurs during a neck surgery. The neck surgery comprises performing a procedure on the subject after covering the portion of the recurrent laryngeal nerve with the shield. The procedure comprises performing surgery on one or more of a thyroid, parathyroid, esophagus, trachea, larynx, pharynx, cervical spine, cervical lymph node, or carotid artery. For example, during a thyroidectomy, the recurrent laryngeal nerve 22 is exposed. The shield 20 will typically be applied promptly after exposure of the recurrent laryngeal nerve 22. This protects the recurrent laryngeal nerve 22 during the remainder of the thyroidectomy and the completion of the neck surgery. In this example, the remainder of the thyroidectomy constitutes the procedure. In some cases, the procedure may be prolonged, e.g., by a neck dissection to remove local lymph nodes. In such cases, the shield 20 protects the recurrent laryngeal nerve 22 throughout (e.g., prevents desiccation and decreases the likeliness of electrical injury or direct instrument trauma during a prolonged procedure). The surgeon refrains from removing the shield 20 from the recurrent laryngeal nerve 22 during the neck surgery and the shield 20 is left in the subject post-surgery.

During the procedure, such as the remainder of the thyroidectomy or any of the other procedures, the surgeon refrains from moving the shield 20 relative to the recurrent laryngeal nerve 22. When placing the shield 20 over the recurrent laryngeal nerve 22, the flared region 38 overlays the external and internal branches 24, 26 of the recurrent laryngeal nerve 22. The narrow region 36 covers a portion of the recurrent laryngeal nerve 22 prior to the branching. The second end edge 30 of the shield 20 extends adjacent the larynx 40. The recurrent laryngeal nerve 22 is in its pre-surgical shape upon being covered. In other words, the recurrent laryngeal nerve 22 is not reshaped (e.g., straightened) before being covered by the shield 20. The shape of the shield 20 also facilitates the placement of the shield 20 while avoiding creases or folds in the shield 20. Further, when placing the shield 20 over the recurrent laryngeal nerve 22, the first curved side 32 and the second curved side 34 follows the curvature of the curved upper aspect of the recurrent laryngeal nerve 22.

In an example of placing the shield 20, a first end margin 44 of the shield 20 is grasped and a second end margin 46 of the shield 20 is grasped. The shield 20 is oriented relative to the recurrent laryngeal nerve 22 such that the second end edge 30 of the shield 20 is adjacent the larynx 40 of the subject and such that the curvature of each of the first 32 and second 34 side edges corresponds to the curvature of the curved upper aspect of the recurrent laryngeal nerve 22. The shield 20 is brought into contact with the recurrent laryngeal nerve 22 such that a portion of the shield 20 contacts the nerve 22 while the grasping of at least one of the two end margins is maintained. For example, a cotton-tip swab is used to press an intermediate portion of the shield 20 to the recurrent laryngeal nerve 22. Next, the grasp on at least one of the two end margins is released. For example, the shield 20 is applied from the intermediate portion outward toward the two opposite ends.

After the recurrent laryngeal nerve 22 is covered, at least partially, by the shield 20, surgery procedure is performed (e.g., the removal of the thyroid in a thyroidectomy) by the surgeon. This allows the shield 20 to protect the recurrent laryngeal nerve 20 throughout the procedure and during any other portion of the operation (e.g., such as a neck dissection for lymph node removal) and/or after the procedure is completed. As such, the shield 20 reduces the chances of damage to the recurrent laryngeal nerve 22 and/or other negative outcomes of the type described herein.

In some embodiments, the shield 20 is left in place at the conclusion of the operation to protect the exposed surface of the recurrent laryngeal nerve from the movement of muscles and other tissues which lay across the exposed surface of the recurrent laryngeal nerve which is subject to trauma from friction during movement of the neck during the healing process. The shield 20 may also prevent scar formation between the recurrent laryngeal nerve and overlying tissues which ordinarily would not be adjacent to the recurrent laryngeal nerve. At the conclusion of the operation, the recurrent laryngeal nerve is exposed and laying upon the top surface of underlying tissues. When the wound is closed, the tissues above are laid down on the recurrent laryngeal nerve and thus the recurrent laryngeal nerve is exposed within the interface of the two tissue bodies. In such a situation, movement of the patient's neck (even minor movement) causes the recurrent laryngeal nerve to be rubbed on and traumatized by the overlying muscles and tissues. This can cause injuries to the recurrent laryngeal nerve during the first 24 hours after the procedure until the tissues begin to stick together and no longer slide relative to each other at the interface between the underlying and overlying tissues. The shield 20 minimizes or prevents such rubbing and may reduce or prevent such injuries.

Although discussed with respect to certain exemplary operations herein, the shield 20 is suitable for use during any operation in which the recurrent laryngeal nerve is exposed. For example, other procedures may include anterior cervical spine fusion, Carotid endarterectomy, central neck dissection for lymph nodes and or cancers of various types, cricopharyngeal myotomy, esophagectomy (cervical approach), excision of Zenker's diverticulum, hemithyroidectomy or other partial thyroidectomy, lateral neck dissection for lymph nodes and/or cancer of various types, modified radical neck dissection (or radical neck dissection), neck biopsy, parathyroidectomy of all forms, partial laryngectomy, substernal goiter resection, and thyroidectomy partial or total.

Also provided herein are methods for covering or contacting a parathyroid gland with a parathyroid gland protective injection. Such parathyroid gland protective injections can comprise liquids or flowable liquids that can be delivered to the parathyroid gland and/or adjacent regions with a syringe or other device. Parathyroid gland protective injections provided herein can be used either alone or in conjunction with a parathyroid shield.

In some embodiments, the parathyroid gland protective injections can comprise delivery of injectable liquid or flowable forms of amniotic tissue around and/or on a parathyroid gland. Suitable forms of injectable amniotic tissue include liquid or flowable forms of extraembryonic tissue (e.g. one or more of human amniotic tissue, human chorionic tissue, non-human amniotic tissue, or non-human chorionic tissue). Suitable forms of injectable amniotic tissue include but are not limited to flowable amniotic membrane allografts that are typically injected into joints are available in in 0.5 cc, 1 cc, and 2 cc vials from various manufacturers (e.g. SurForce®, Surgenex, Scottsdale, Arizona, 85260) and can be adapted for use in the methods for protecting parathyroid glands provided herein.

In some embodiments, the parathyroid gland protective injections can comprise delivery of stem cell, a stem cell exudate, or a combination thereof around and/or on a parathyroid gland. In some embodiments, the stem cell and/or stem cell exudate is an autologous stem cell and/or an autologous stem cell exudate. In some embodiments, the stem cell and/or stem cell exudate is an allogeneic stem cell and/or an allogeneic stem cell exudate. Non-limiting examples of autologous or allogenic stem cells and stem cell exudates include bone marrow, molar, peripheral blood, adipose, amniotic fluid, and umbilical cord blood stem cells and stem cell exudates. Stem cell exudates that can be used include stem cell conditioned media and components thereof. Stem cell conditioned media can be obtained by culturing the stem cells in media from about 16 hours to about five days (Pawitan J A. 2014; 2014:965849. doi: 10.1155/2014/965849). In certain embodiments, the stem cell exudate comprises one or more growth factors, cytokines, and/or anti-inflammatory agents. Such growth factors include but are not limited to VEGF, FGF2, EGF, HGF, PlGF, SDF-1, PDGF, TGF-beta1, and PDEGF (Ibid). Such cytokines include but are not limited to IL-8, IL-9, UPA, thrombospondins 1 and 2, serpin E-1, SDF-1, TIMP-1, IGFBP, ADM, and DKK 1 (Ibid). Antiinflammatory agents include but are not limited to IL-10, IL-1ra, IL-13 and IL-27 (Zagoura et al. Gut. 2012 June; 61(6):894-906. doi:10.1136/gutjnl-2011-300908).

The covering or contacting of the parathyroid gland can occur during a neck surgery (e.g., following a thyroidectomy or during or following a parathyroid surgery) or in reconstructive surgery (e.g., following an injury to the neck). The neck surgery procedures where the parathyroid gland can be covered or contacted as disclosed herein can comprise performing surgery on one or more of a thyroid, parathyroid, esophagus, trachea, larynx, pharynx, cervical spine, cervical lymph node, or carotid artery. For example, during a thyroidectomy and during parathyroid surgery, the parathyroid glands exposed and/or perturbed. The parathyroid shield and/or parathyroid gland protective injection can be applied at any stage during the procedure but is most typically performed once actions that will expose and/or perturb the parathyroid gland are complete (e.g., after a thyroidectomy or after commencement of the procedure on the thyroid). In some embodiments, the parathyroid is covered or contacted by a step comprises laying the layer of extraembryonic tissue over the parathyroid gland. In some embodiments, the covering or contacting of the parathyroid glands comprises injecting parathyroid gland protective injection (e.g., with extraembryonic tissue, stem cells, stem cell exudates, and/or any combination thereof) on and/or adjacent the parathyroid gland. In some embodiments, the parathyroid gland that is covered or contacted is ischemic or pre-ischemic. In some embodiments, the parathyroid gland(s) are removed and autotransplanted to another location and covered or contacted and the shield or injected material is left in the subject post-surgery. In some embodiments, the parathyroid gland is left in situ (e.g. is not transplanted) during the surgery and covered or contacted with the parathyroid shield and/or parathyroid gland protective injection. In some embodiments, the surgeon refrains from removing the parathyroid gland shield or parathyroid gland protective injection from the parathyroid gland during the neck or reconstructive surgery and the shield or injected material is left in the subject post-surgery. In certain embodiments, the subject's parathyroid function as measured by parathyroid hormone (PTH) levels and serum calcium levels is monitored before surgery to establish a baseline PTH and calcium levels and/or at various intervals post-surgery (e.g., at about 1, 2, 3, or more months post-surgery). It is anticipated that subjects receiving a parathyroid shield and/or a parathyroid gland protective injection will return to baseline or near baseline levels of parathyroid function (e.g., at least about 50%, 75%, or 90% of baseline PTH and calcium levels) more quickly (e.g., within about 1, 2, 3, or more months post-surgery) in comparison to control cohort subjects who have undergone similar procedures but have not received a parathyroid shield and/or a parathyroid gland protective injection.

In view of the foregoing, it will be seen that the several advantages of the disclosure are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method comprising:
   performing a neck surgery on a subject;
   during the neck surgery, performing a thyroid procedure or a parathyroid procedure on the subject;
   during the neck surgery, covering a parathyroid gland of the subject with extraembryonic tissue, wherein the parathyroid gland is ischemic during the covering of the parathyroid gland with extraembryonic tissue,
   wherein the covering of the parathyroid gland with the extraembryonic tissue occurs after commencement of the thyroid procedure or the parathyroid procedure.

2. The method as set forth in claim 1 wherein the performing comprises performing a thyroidectomy, and wherein the covering of the parathyroid gland with the extraembryonic tissue occurs after the thyroidectomy.

3. The method as set forth in claim 1 further comprising refraining from removing the extraembryonic tissue from the subject during the neck surgery such that the extraembryonic tissue is in the subject post-surgery.

4. The method as set forth in claim 1 wherein the extraembryonic tissue comprises a layer of extraembryonic tissue, and wherein the covering step comprises laying the layer of extraembryonic tissue over the parathyroid gland.

5. The method as set forth in claim 1 wherein the covering of the parathyroid gland with the extraembryonic tissue comprises injecting the extraembryonic tissue on and/or adjacent the parathyroid gland.

6. The method as set forth in claim 1 wherein the parathyroid gland is in-situ during the covering of the parathyroid gland with the extraembryonic tissue.

7. The method as set forth in claim 1, wherein the performing comprises performing the parathyroid procedure, and wherein the parathyroid procedure comprises removing the parathyroid gland from its original location and auto-transplanting the parathyroid gland.

8. The method as set forth in claim 1 wherein the extraembryonic tissue comprises one or more of human amniotic tissue, human chorionic tissue, non-human amniotic tissue, or non-human chorionic tissue.

9. The method as set forth in claim 1 wherein the extraembryonic tissue comprises amniotic tissue and chorionic tissue.

10. The method as set forth in claim 1 further comprising contacting the parathyroid gland with a stem cell, a stem cell exudate, or a combination thereof.

11. The method as set forth in claim 10 wherein the stem cell and/or stem cell exudate is an autologous stem cell and/or an autologous stem cell exudate.

12. A method comprising:
performing a neck surgery on a subject;
during the neck surgery, performing a thyroid procedure or a parathyroid procedure on the subject;
during the neck surgery, contacting a parathyroid gland of the subject with extraembryonic tissue, wherein the parathyroid gland is ischemic during the contacting of the parathyroid gland with extraembryonic tissue,
wherein the contacting of the parathyroid gland with the extraembryonic tissue comprises injecting the extraembryonic tissue adjacent the parathyroid gland, and wherein the extraembryonic tissue is a liquid during the contacting of the parathyroid gland with the extraembryonic tissue.

13. The method as set forth in claim 12 wherein the parathyroid gland is in-situ during the contacting step.

14. The method as set forth in claim 12, further comprising removing the parathyroid gland from its original location and auto-transplanting the parathyroid gland.

15. The method as set forth in claim 12 wherein the extraembryonic tissue comprises one or more of human amniotic tissue, human chorionic tissue, non-human amniotic tissue, or non-human chorionic tissue.

16. The method as set forth in claim 12 wherein the extraembryonic tissue comprises amniotic tissue and chorionic tissue.

17. The method as set forth in claim 16 wherein the parathyroid gland is in-situ during the contacting step.

18. The method as set forth in claim 12 further comprising contacting the parathyroid gland with a stem cell, a stem cell exudate, or a combination thereof.

19. The method as set forth in claim 18 wherein the stem cell and/or stem cell exudate is an autologous stem cell and/or an autologous stem cell exudate.

20. A method comprising:
performing a neck surgery on a subject;
during the neck surgery, performing a thyroid procedure or a parathyroid procedure on the subject;
during the neck surgery, contacting a parathyroid gland of the subject with a stem cell, wherein the parathyroid gland is in-situ during the contacting of the parathyroid gland with the stem cell.

21. The method as set forth in claim 20 wherein the parathyroid gland is ischemic during the contacting of the parathyroid gland with the stem cell.

22. The method as set forth in claim 21 wherein the stem cell is an autologous stem cell.

23. The method as set forth in claim 21 wherein the stem cell is an adipose, molar, peripheral blood, amniotic fluid, umbilical cord blood, or bone marrow stem cell.

24. The method as set forth in claim 20 further comprising refraining from removing the stem cell from the subject during the neck surgery such that the stem cell is in the subject post-surgery.

25. The method as set forth in claim 20 wherein the subject's parathyroid hormone (PTH) and serum calcium levels are monitored before contacting the parathyroid gland of the subject with the stem cell and/or at various intervals after contacting the parathyroid gland with the stem cell and wherein the subject's PTH and serum calcium levels return to baseline or near baseline levels more quickly in comparison to control cohort subjects who have undergone thyroid or parathyroid procedures without a stem cell contacting a parathyroid gland.

\* \* \* \* \*